United States Patent
Kamen et al.

(10) Patent No.: US 6,375,459 B1
(45) Date of Patent: *Apr. 23, 2002

(54) APPARATUS AND METHOD FOR CLEANING TEETH

(75) Inventors: Dean L. Kamen, Bedford; Larry B. Gray, Merrimack; Mark D. Newton, Dunbarton, all of NH (US)

(73) Assignee: Deka Products Limited Partnership, Manchester, NH (US)

( * ) Notice: Subject to any disclaimer, the term of this patent is extended or adjusted under 35 U.S.C. 154(b) by 39 days.

This patent is subject to a terminal disclaimer.

(21) Appl. No.: 09/632,685

(22) Filed: Aug. 7, 2000

Related U.S. Application Data

(63) Continuation-in-part of application No. 09/280,144, filed on Mar. 26, 1999, now Pat. No. 6,155,824.
(60) Provisional application No. 60/079,502, filed on Mar. 26, 1998.

(51) Int. Cl.$^7$ .................................................. A61C 17/02
(52) U.S. Cl. ............................ 433/80; 604/35; 601/162
(58) Field of Search ......................... 433/80, 88, 89, 433/116; 604/27, 35; 601/162–165; 451/75, 90

(56) References Cited

U.S. PATENT DOCUMENTS

| | | | |
|---|---|---|---|
| 3,065,749 A | * 11/1962 | Brass | |
| 3,211,149 A | * 10/1965 | Fono | |
| 3,452,746 A | * 7/1969 | Shanhouse | |
| 4,020,596 A | * 5/1977 | Bergh | |
| 4,096,241 A | * 6/1978 | Geistlich et al. | 424/54 |
| 4,111,193 A | * 9/1978 | Jousson | |
| 4,540,365 A | * 9/1985 | Nelson et al. | 433/88 |
| 4,692,140 A | * 9/1987 | Olson | 604/40 |
| 4,776,794 A | * 10/1988 | Meller | 433/216 |
| 4,801,292 A | * 1/1989 | Watson | 604/36 |
| 4,903,688 A | * 2/1990 | Bibby et al. | |
| 4,941,459 A | * 7/1990 | Mathur | |
| 4,952,392 A | * 8/1990 | Thame | 424/58 |
| 4,961,923 A | 10/1990 | Heyde | 424/49 |
| 5,057,309 A | 10/1991 | Hill et al. | 424/52 |
| 5,088,515 A | * 2/1992 | Kamen | 137/15 |
| 5,145,367 A | * 9/1992 | Kasten | 433/84 |
| 5,286,192 A | * 2/1994 | Dixon | 433/80 |
| 5,321,865 A | * 6/1994 | Kaeser | 15/22.1 |
| 5,328,682 A | * 7/1994 | Pullen et al. | 424/49 |
| 5,460,604 A | * 10/1995 | Arnett et al. | 604/35 |
| 5,542,918 A | * 8/1996 | Atkinson | 604/27 |
| 5,547,376 A | * 8/1996 | Harrel | 433/116 |
| 5,564,629 A | * 10/1996 | Weissman et al. | 239/8 |
| 5,634,791 A | * 6/1997 | Matsuuda et al. | 433/87 |
| 5,801,226 A | 9/1998 | Cummins et al. | 530/388.2 |
| 5,855,869 A | 1/1999 | Domke et al. | 424/49 |
| 6,155,824 A | * 12/2000 | Kamen et al. | 433/80 |

FOREIGN PATENT DOCUMENTS

| | | |
|---|---|---|
| FR | 2 455 456 | 11/1980 |
| FR | 2 588 469 | 4/1987 |

OTHER PUBLICATIONS

Equipment Profile for Micadent II, Medidente International, Inc., http://www.medidenta.com/equip/micadent/index.html.

* cited by examiner

Primary Examiner—Ralph A. Lewis
(74) Attorney, Agent, or Firm—Bromberg & Sunstein LLP

(57) ABSTRACT

An apparatus designed to clean surfaces and to recycle a cleaning fluid. The apparatus has a hand-holdable housing that includes a head with a distal end through which cleaning solution may be impelled. The apparatus further has a pump for both impelling and urging cleaning fluid back through a return path. The pump has a flexible membrane and a pump drive mechanism in which two pistons drive the flexible membrane. The cleaning fluid includes a foaming-resistant composition that has an abrasive agent; a shear thinning fluid matrix, and a non-foaming means.

26 Claims, 5 Drawing Sheets

APPARATUS AND METHOD FOR CLEANING TEETH

RELATED U.S. APPLICATIONS

The present application is a continuation-in-part of U.S. patent application Ser. No. 09/280,144, filed Mar. 26, 1999, now U.S. Pat. No. 6,155,824 which claims priority from Provisional Application Serial No. 60/079,502, filed Mar. 26, 1998, both of which applications are hereby incorporated by reference herein.

TECHNICAL FIELD

The present invention relates to devices, methods, and compositions for cleaning surfaces within a person's mouth.

BACKGROUND ART

It is well known that solutions containing baking soda or other abrasive materials serve as excellent media for cleaning teeth. There are many known devices which provide delivery of such solutions for purposes of oral hygiene. These devices are typically large complicated systems intended for professional use in a dentist's office. The terms "solution" and "cleaning fluid" will be used interchangeably within this description and the appended claims to refer to any fluid, suspension, or slurry that may be used, as the application dictates, for cleaning a surface.

SUMMARY OF THE INVENTION

The invention provides an apparatus designed to pump an appropriate amount of solution into the mouth of a user in order to clean teeth and to recycle that fluid for its reuse by an individual. In accordance with an embodiment of the invention, the apparatus includes a base component and a head component, attachable to each other to form a hand-holdable unit, a flexible membrane, and a pump drive mechanism. The pump drive mechanism is disposed within the base component and drives the flexible membrane in such a manner as to impel a cleaning fluid toward a surface and to return the cleaning fluid from the vicinity of the surface to the head component.

DESCRIPTION OF SPECIFIC EMBODIMENTS

Figure 1:
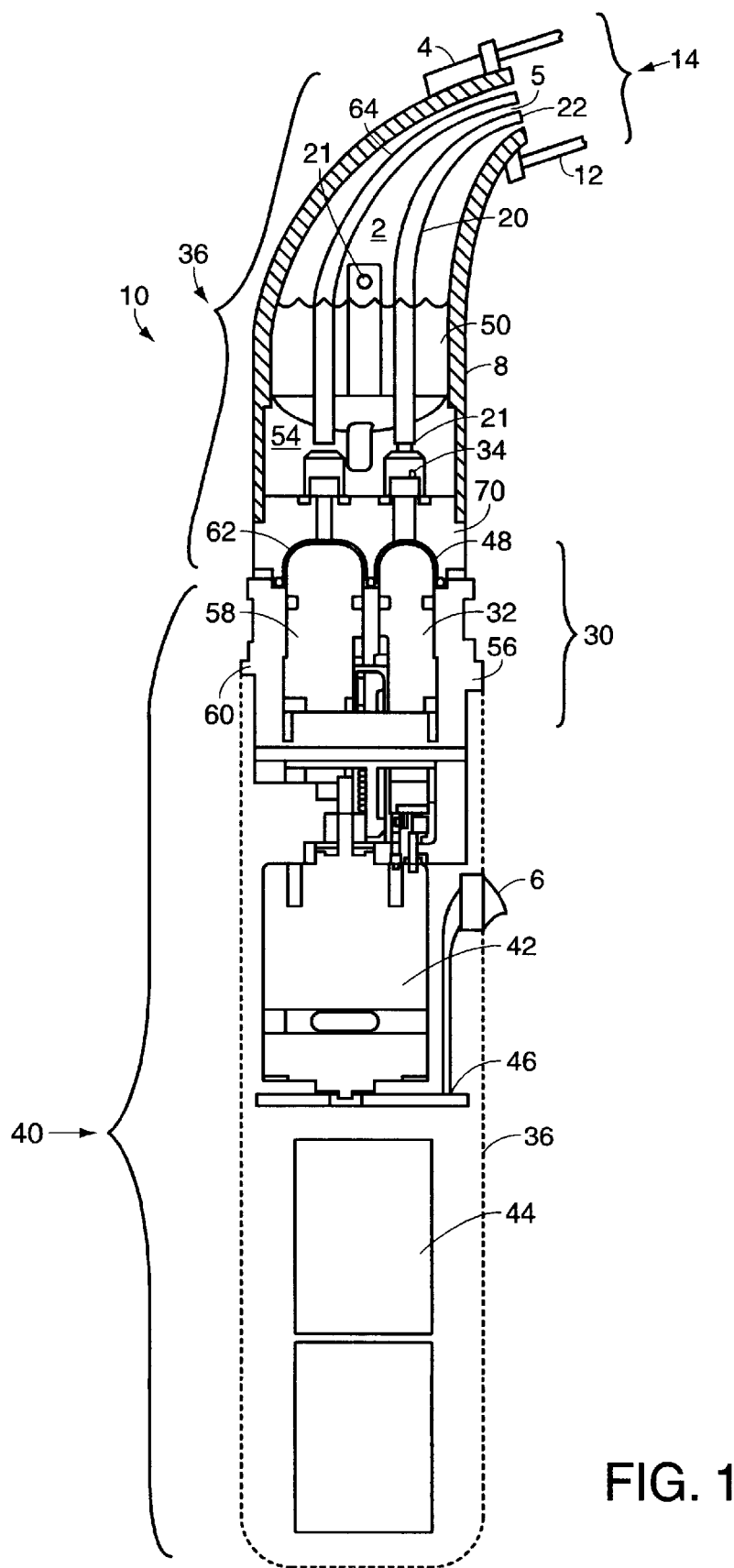
FIG. 1 is a longitudinal sectional view of an assembled apparatus for cleaning teeth according to an embodiment of the invention utilizing separable head and handle components.

An embodiment of an apparatus to clean teeth including a hand-holdable housing 10, a high-pressure jet tube 20, and a pump 30, is shown in FIG. 1. In the present description, end 21 of tube 20 coupled to pump 30 is referred to as the proximal end of the tube. Pump 30 displays sufficient pumping capacity, in accordance with the various embodiments described below, to both impel a cleaning solution (or slurry) 50 out of distal opening 14 and urge (or draw) solution back into distal opening 14 so as to recycle the cleaning solution. Preferred mechanisms for actuating pump 30 are discussed below, however the present invention is in no way limited to any particular type of pump.

Referring further to FIG. 1, hand-holdable housing 10 includes two separable component parts: head 36 and handle (or base) 40. Head 36 contains a reservoir of slurry 50 and is hygienically suited for individual use. Head 36 may be readily attached to base 40 for use by a particular user. Base 40, which may thus be used in common among various users, contains a motor 42 for actuating pump 30 as well as power source 44 and associated electronics 46. Switch 6 is conveniently disposed on base unit 40 so that a user may conveniently turn the apparatus on and off. Solution is impelled by high-pressure piston 32 of pump 30, acting within highpressure cylinder 56 to drive membrane 48 against cylinder head 70 of head unit 36 and thus to impel the solution through one-way valve 34, into tube 20, so as to exit at a distal end 22 of the tube. Distal end 22 of tube 20 forms an exit nozzle. Solution from the vicinity of the surface to be cleaned is then drawn in return into a reservoir volume 54 by action of vacuum piston 58 in a second cylinder 60.

Vacuum piston 58 expels air into a air tube 64 from plenum 2 that sits above the level of slurry 50 in the reservoir. The air jet from air tube 64 also helps in cleaning teeth in combination with the solution jet ejected from distal end 22 of tube 20. By drawing air from plenum 2 via vacuum inlet 21, vacuum pump 58 creates a partial vacuum in the plenum space 2. The vacuum created in plenum space 2 creates a return pressure gradient such that used solution from the mouth returns to reservoir 50 via the opening 5 between air tube 64 and solution tube 20.

Pump 30 drives membrane 48 which serves to seal cleaning slurry 50 within head 36. Base 40 is encased by shell 36 to facilitate comfortable hand-held use. In accordance with various embodiments of the invention, distal opening 14 of head 36 may be lined with brush bristles 12 or, alternatively, may be terminated in an orifice boot (not shown). A dynamic supply of cleaning slurry 50 is preferably maintained within head 36 in a reservoir volume 54, otherwise referred to as a "bowl." Forward fluid communication is defined as maintaining a path for cleaning solution to flow from one-way valve 34 to the vicinity of a surface to be cleaned. Return fluid communication is similarly defined as maintaining a path for cleaning solution to be urged from the vicinity of the surface to be cleaned and returned to housing 10. For embodiments which include a reservoir 54, forward fluid communication is that communication directed away from the reservoir 54 and return fluid communication is directed toward the reservoir 54.

In accordance with alternate embodiments of the invention, a sensor 4 may be strategically placed to automatically effectuate activation of the apparatus. By way of examples, a pressure sensor in the exit nozzle 22 may be included in order to activate the apparatus in the case when the exit nozzle 22 or bristles 12 contact a surface. Alternatively, a photo sensor may be used to activate the apparatus when the exit nozzle 22 is placed into the mouth of a user, causing a reduction in sensed light.

In accordance with embodiments of the invention, faring 8 of head unit 36, as well as tube 20 and pump 30 may be manufactured from a material transparent to and capable of being sterilized by ultraviolet radiation. A suitable material is a synthetic polymer, which polymer can be an ionomer, a polycarbonate, or a polyethylene. A suitable ionomer is an ethylene/methacryclic acid copolymer, for example, Surlyn®. A suitable polycarbonate is Lexan®, having great clarity and stability. In another embodiment, the material can be sterilized by heating for an effective period of time in a microwave oven.

Figure 2:
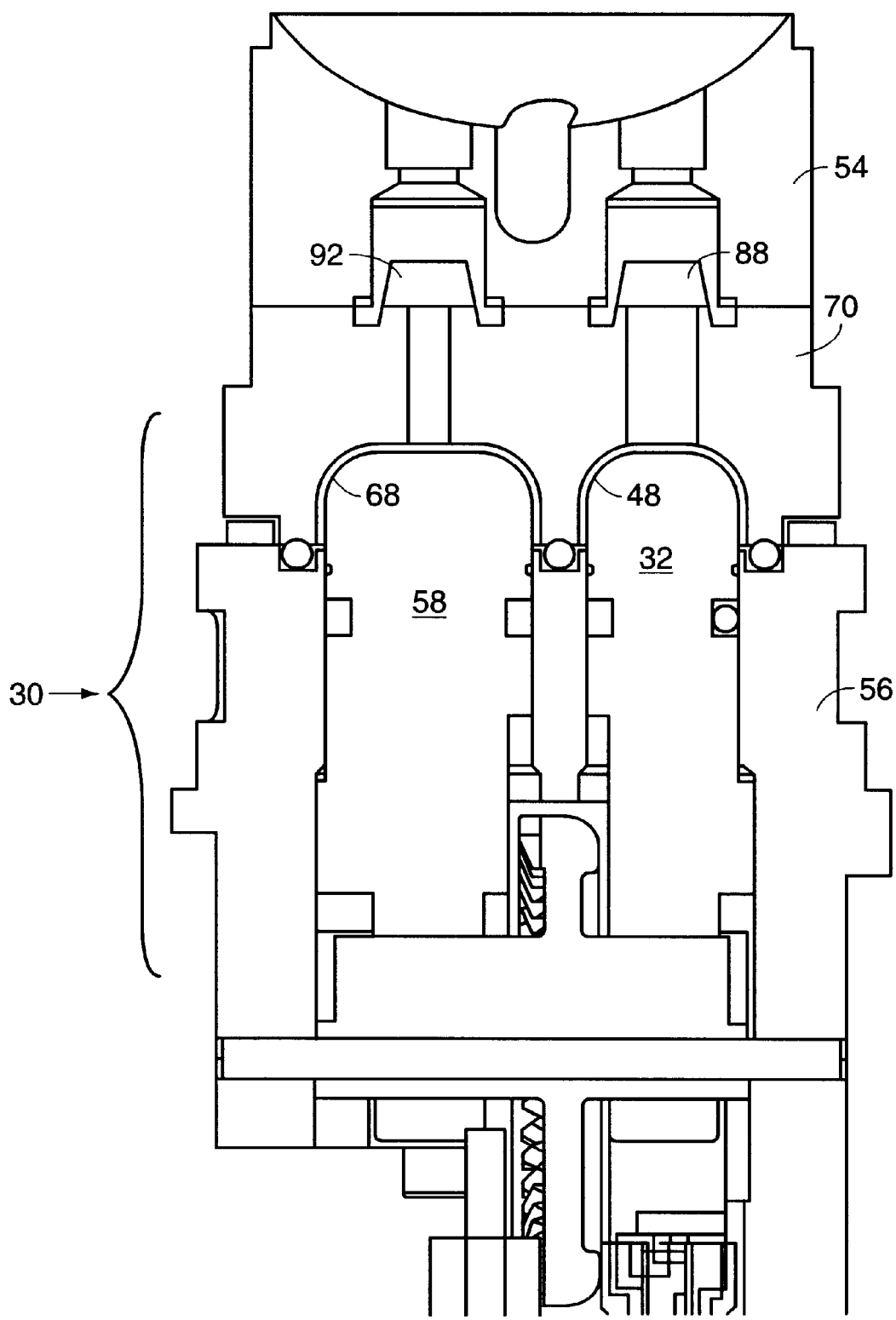
FIG. 2 is a sectional view of a dual-cylinder pump for application in conjunction with the tooth cleaning apparatus of FIG. 1.
Figure 3:
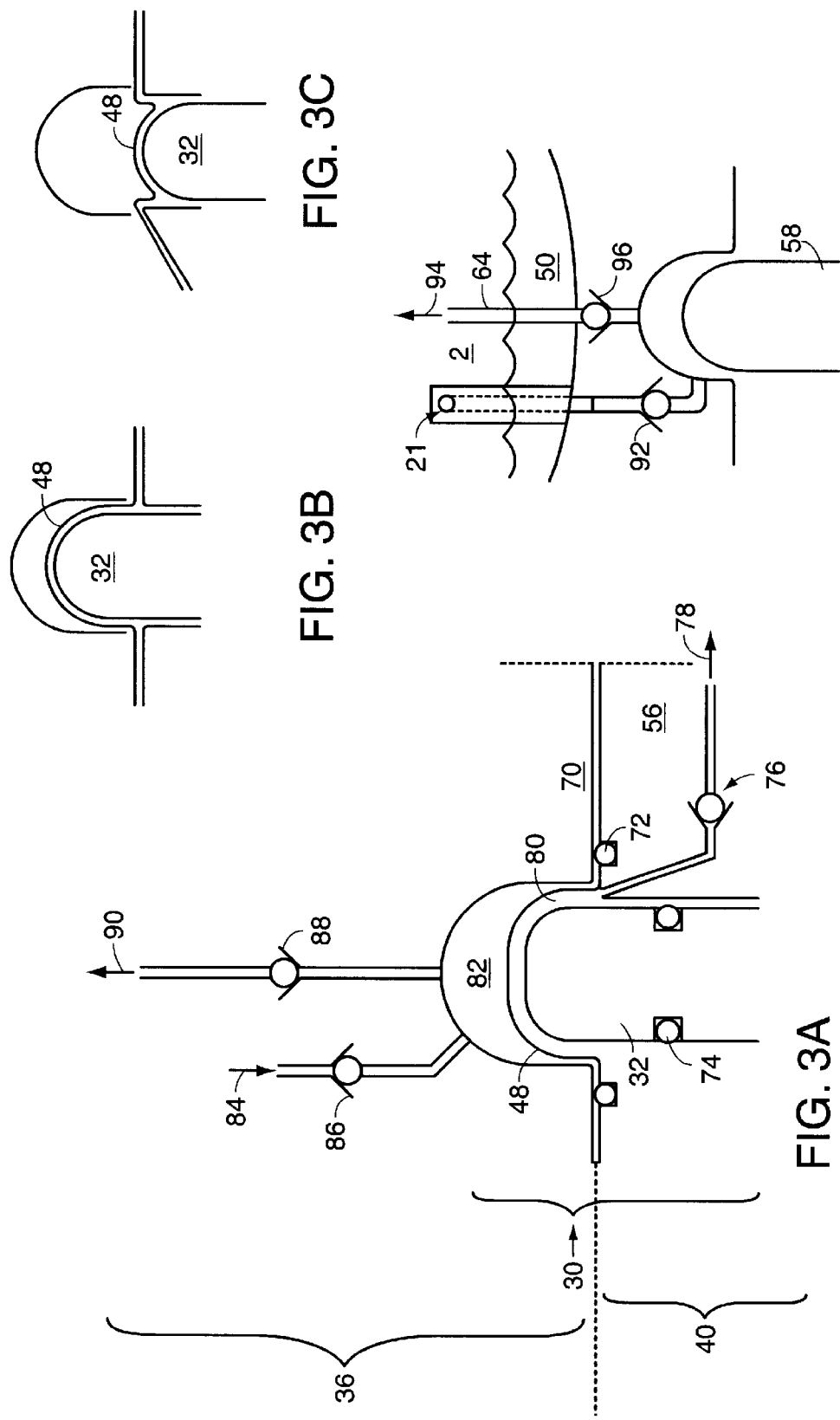
FIGS. 3A, 3B and 3C are schematic representations of membrane-based pumping by the high pressure piston and associated fluid flow in accordance with an embodiment of the invention.
FIG. 3D is schematic representations of membrane-based pumping by the vacuum piston and associated fluid flow in accordance with an embodiment of the invention.

Operation of pump 30 is now more particularly described with reference to FIGS. 2–5. FIG. 2 shows a cross-sectional view of the central portion of the apparatus of FIG. 1, enlarged to show pump 30 in greater detail. Membrane 48, driven by high-pressure piston 32, and membrane 68, driven by vacuum piston 58, may be formed of a single sheet of material such as an elastomer and preferably polyurethane. Together, membranes 48 and 58 serve as a barrier retaining the entire volume of recycled fluid within head 36 and preventing contact between the fluid and pump mechanisms that are common to multiple users of the device.

Initial operation of the pump is discussed in reference to the more detailed cross-sectional view of the membrane interface as shown in FIGS. 3A–3D. Membrane 48 is sealed, with respect to the flow of fluid or air, to both a cylinder head 70 (shown in FIGS. 2 and 3A), comprising a portion of head segment 36, and to cylinder 56. The seal is preferably provided by an figure-eight-type seal 72, shown most clearly in FIG. 5.

Referring to FIG. 3A, upon coupling of head segment 36 to base 40, air is initially trapped between piston 32 and membrane 48, since the volume 80 bounded by the piston and membrane is sealed by O-ring 72 and piston seal 74. In order to initiate operation of pump 30, one-way valve 76 allows air to be purged via path 78. After air pocket 80 has been purged, membrane 48 tracks the reciprocating motion of piston 32 between the retracted position, shown in FIG. 3C, and the extended position, shown in FIG. 3B.

Volume 82, bounded by membrane 48 and cylinder head 70 constitutes the "fluid chamber" of pump 30. On the downstroke of piston 32, membrane 48 is retracted, and cleaning slurry is drawn into fluid chamber 82 in direction 84 via one-way valve 86. On the upstroke of piston 32, fluid is urged from fluid chamber 82 via one-way valve 88 in direction 90 toward the surface to be cleaned.

Referring again to FIG. 2, piston 58 may be driven out-of-phase with piston 32, thereby providing for the drawing of a vacuum, through one-way valve 92, using the identical mechanism described above with regard to the impelling high-pressure piston 32. FIG. 3D shows vacuum piston 58 in a partially retracted position. A downstroke of piston 58 draws in air, via one-way valve 92, from inlet 21 situated above slurry 50, thereby creating a partial vacuum in plenum space 2 above the slurry. The upward stroke of piston 58 creates an air jet 94, via one-way valve 96, that contributes to cleaning the teeth in combination with the solution jet previously described.

Figure 4:
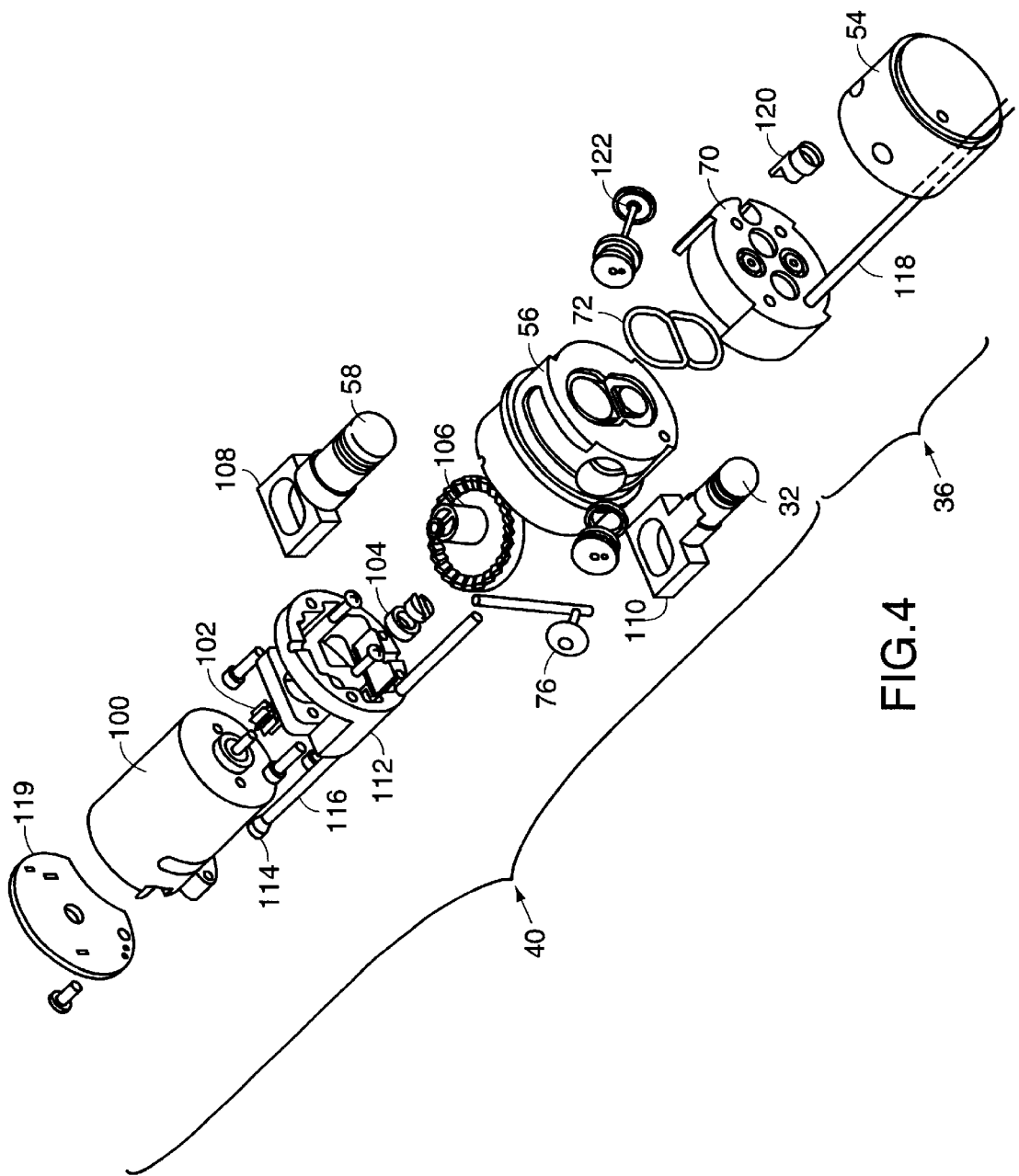
FIG. 4 is an exploded perspective view of the drive train for actuating a dual-chambered pump in accordance with an embodiment of the invention.

A preferred embodiment for driving the dual pistons 32 and 58 is now described with reference to FIG. 4. The drive components are contained within handle unit 40. Electric motor 100 drives both high-pressure piston 32 and vacuum piston 58 via a drive train that, in a preferred embodiment, includes pinion gear 102, idler 104, face gear and cam unit 106, the cam driving the respective pistons by means of Scotch yokes 108 and 110. The aforesaid drive components are shown by way of example, and different drive trains known to persons skilled in the mechanical arts may be employed to drive the pistons 32 and 58. Mating of cylinder 56 to gear housing 112 is also shown in FIG. 4, as is light sensor 114 which precludes operation of motor 100 and the piston drive chain unless cylinder head 70 of head segment 36 as been secured to cylinder 56 of handle unit 40. Light pipe 116 transmits light to sensor 114, preventing, via circuitry of circuit board 118, activation of motor 100 if light reaches the sensor. A second light pipe 118 transmits light from the distal end of the head to the first light pipe. The motor is only enabled when light is diminished as the device is inserted into the mouth of the user.

One-way valve 76 is associated, as described above, with initial purging of the air pocket behind membrane 48. One-way valve 122 is an air vent valve associated with the vacuum piston, for initial purging of the air pocket behind membrane 62 in a corresponding manner.

Figure 5:
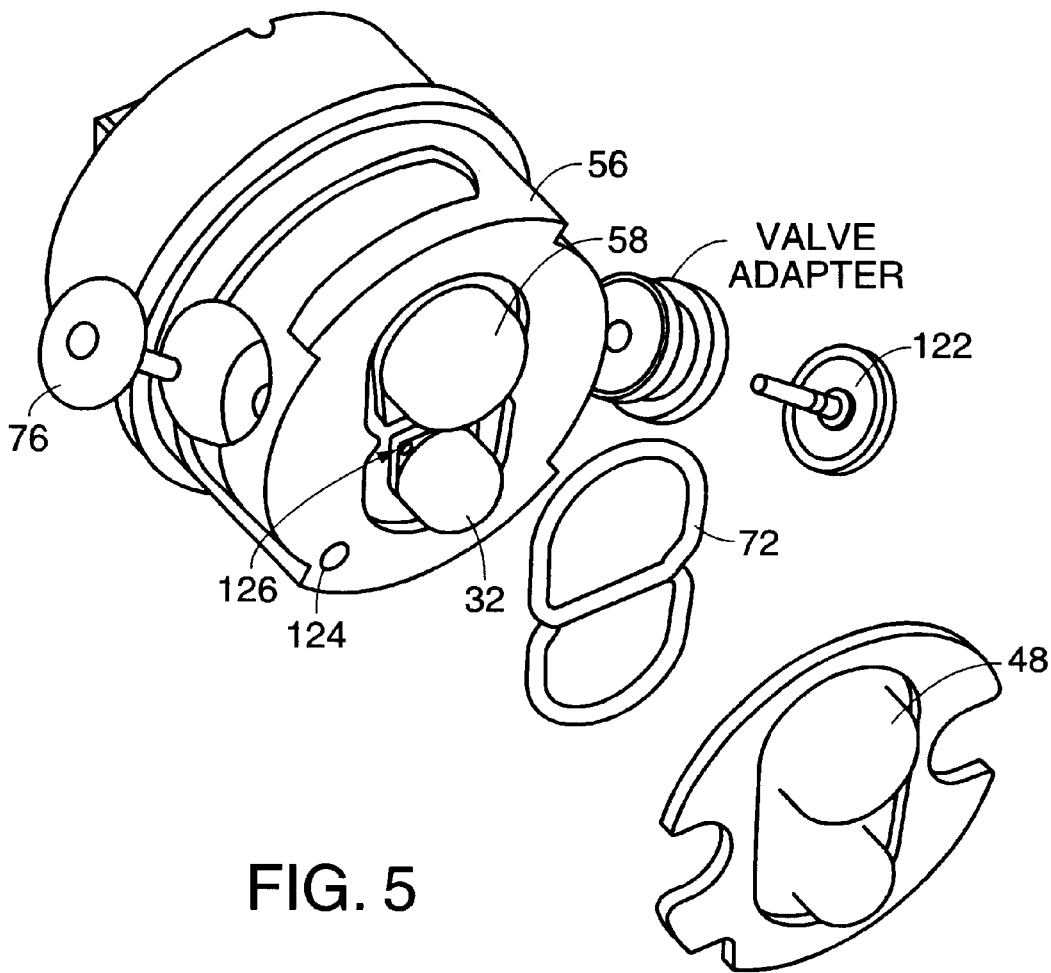
FIG. 5 shows an exploded view of the pistons and membrane of the dual cylinder pump of FIG. 2.

FIG. 5 shows an exploded perspective view of cylinder 56 and associated components. Membrane 48 (shown in FIGS. 1 and 2) has been omitted for clarity. High pressure piston 32 and vacuum piston 58 are shown in dual cylinder 56, while corresponding one-way air vent valves 122 and 76 are shown in exploded positions. Aperture 124 provides for light to pass through cylinder block 56 via light pipe 118 to light pipe 116 (both shown in FIG. 4). Vent hole 126 is the opening to air vent valve 76 that purges the air between the membrane and the piston.

Alternate embodiments of the invention are now described with reference to FIGS. 6–8. FIGS. 6A and 6B illustrate the flow of solution from the reservoir 12, through a physically distinct inlet valve 33, pumping chamber 35, and exit valve 34. A representation of control fluid flow is also illustrated. FIGS. 7A and 7B illustrate designs for an inlet or exit valve according to an embodiment of the invention. These valves may be of the type disclosed in U.S. Pat. No. 5,088,515 for an invention of Kamen, which patent is incorporated herein by reference. FIGS. 8A and 8B show yet a further alternate valve design. Either of these designs, as well as others within the spirit of the invention, may be incorporated into the pump represented in FIGS. 6A and 6B. Fluid enters the valves of FIGS. 6A and 6B and FIGS. 7A and 7B at entry 130 and exits the valves at exit 132.

In the embodiment of the valve design of FIGS. 7A and 7B, a second flexible membrane 42 is shown to be in contact with the first flexible membrane 32. In this design, solution allowed to enter entry 130, flows into a region 36, and is then forced out of region 36 into exit 132. FIGS. 7A and 7B show the two extremal positions of the flexible membranes.

In the embodiment of the valve design of FIGS. 8A and 8B, membrane 32 is used to force a cone-shaped valve part 37 toward and away from a mating cavity defined by the body of the pump 30. This design may advantageously provide superior valve seating and increased impelling and urging force.

Methods of cleaning a surface in an oral cavity by actuating a pump 30, such as those described above, including both impelling solution to a vicinity of a tooth surface, and holding an exit nozzle 22 to urge the recycling of that solution, provide additional embodiments of the present invention.

An embodiment of the invention is a fluid formulation for use in a device that recirculates fluid for the cleaning of surfaces in the oral cavity of the mouth, such as the surfaces of teeth and gums. The requirements of the devices herein include a low viscosity, non-foaming fluid matrix, containing abrasive particles which are not harmful to enamel. As used in this description and in any appended claims, "non-foaming" refers to a liquid which foams, if at all, to a degree insufficient to substantially inhibit the flow of fluid through the system. Omission of a foaming detergent, or use of a foam suppressor, or addition of a non-forming detergent, and addition of an abrasive material to the fluid, together produce an oral cleansing fluid that facilitate the operation of a recirculating hydraulic oral cleansing device.

Prior art dentifrice and mouthwash formulations comprise detergents such as mono and disodium laurel sulfates as essential ingredients to effect a lower surface tension, thereby helping to loosen plaque deposits and to suspend debris removed from the tooth surface during cleaning. Further, detergents create a desired foaming effect in the mouth when agitated. Low viscosity products such as dental rinses and mouthwash do not contain abrasive or suspended particles. A low viscosity fluid preferably contains suspended particles abrasive to the surface that does not foam when agitated.

Pet toothpastes and human infant toothpastes are formulated without detergents to avert digestive tract irritation brought on by swallowing the dentifrice. For humans, detergents such as mono and disodium laurel sulfate are included primarily because of a strong consumer preference for the mouth-feel of the resultant foaming action. Prior art employing abrasives in "liquid" formulations are designed to exhibit sufficient low viscosity to maintain stability and achieve a satisfactory degree of "brush hold" when dispensed (between 50 and 1,500 Pa·s at a shear rate of 0.1 $sec^{-1}$ is typical). Pullen et al. U.S. Pat. No. 5,328,682 (1994), which is incorporated herein by reference, describes an abrasive mouthwash which includes detergent as an essential ingredient in order to produce a foam upon use.

Preferable elements of the oral cleaning fluid include: a low viscosity Newtonian or non-Newtonian (shear thinning) fluid matrix or combination of fluids (1–2000 cP, present in an amount that is from about 60 to about 100% of the total composition) such as water or an alcohol such as ethanol; an abrasive with a hardness between that of dentin (1.0–1.5 Mohs) and that of enamel (5.5–8.0 Mohs), present in an amount that is from about 0.01 to about 40% of the composition, and a non-foaming formulation. Abrasives that may be used may include chalks, silicas and silicates, hydrated aluminas and aluminosilicates, calcium carbonate, magnesium carbonate, magnesium trisilicate, magnesium hydroxide, hydroxyapatites, trimetaphosphates, monomorillonite, hectorite and various alkali metal phosphates such as dicalcium phosphate dihydrate or sodium metaphosphate, or various synthetic resins.

The non-foaming formulation may be achieved by combining a detergent or surfactant with a defoaming agent, by employing a non-foaming detergent or a surfactant, or by formulating the mixture in the absence of a detergent or surfactant. A nonionic surfactant is preferred to lower surface tension with minimal foaming.

Ranges of a shear thinning fluid content in the formulation can include an amount that is greater than about 60% of the composition and is preferably in the range of 80–97% of the composition. Ranges of abrasive content in the formulation can include: from about 0.1 to about 40% of the composition, and preferably between 2–20% of the composition.

Additional optional elements of this embodiment of the invention may include a suspension agent such as a colloidal magnesium aluminum silicate, natural or synthetic clays, or organic dispersing agents; a viscosity modifier or humectant such as sorbitol; a stabilizer such as propylene glycol; a defoamer such as mineral oil; salts or pH buffers; a preservative such as sodium benzoate; a color, a flavor, and a sweetening enhancing agent; and a variety of therapeutic agents. The therapeutic agents may include decay preventatives such as fluorides, sensitivity reduction agents such as potassium nitrate and strontium chloride, tartar control agents such as pyrophosphates, whitening agents such as hydrogen peroxide, bleaching and stain-removing enzymes (e.g., glucose, oxidase, protase, mycleoperoxidease) and plaque inhibitors such as enzymatic hypothiocyanate and 2,4,4'-trichloro-2'-hydroxy diphenyl ether. Antibacterial agents and anti-inflammatory agents may also be included.

The invention is designed to be safe for oral use and potential or occasional inadvertent ingestion.

One sample composition, provided solely by way of example, contains 9.0% (by weight) silicon dioxide, 325 mesh, 0.1% magnesium aluminum sulfate, 0.3% xanthan gum, 0.1% coloring; 0.4% sweetener, 0.3% flavoring, and the balance, water. It is to be understood that to the extent to which changes in the composition do not materially alter the final product they are to be considered as falling within the spirit and scope of the exemplary embodiment described.

The invention is designed specifically to be used advantageously in conjunction with a device that can jet the fluid onto the teeth and gums to provide the necessary inertia to clean the enamel surface on a tooth and to clean and stimulate a surface of the gums. The fluid is optimally designed to be used in devices that jet and recirculate the fluid but may also be used by those that simply jet the fluid into the oral cavity followed by expulsion from the mouth by the user.

Although the invention has been described with reference to several preferred embodiments, it will be understood by one of ordinary skill in the art that various modifications can be made without departing from the spirit and the scope of the invention, as set forth in the appended claims.

We claim:

1. An apparatus for cleaning a surface, the apparatus comprising:
   a hand-holdable housing having a base component and a head component, the head component detachably coupled to the base component at a proximal end and also having a distal end;
   a flexible membrane retaining a cleaning fluid composition within the head component of the housing;
   a pump drive mechanism disposed within the base component of the housing for driving the flexible membrane, the membrane having a substantially planar dimension the pump drive mechanism and the flexible membrane comprising a pump, in such a manner as to impel the cleaning fluid composition toward the surface and to return the cleaning fluid from the vicinity of the surface to the head component.

2. An apparatus according to claim 1, wherein the head component further includes a reservoir for retaining the cleaning fluid composition both before it is impelled by the pump and after it is returned by the pump, the membrane preventing contact between the fluid and the pump drive mechanism, so that urged fluid is capable of being impelled.

3. An apparatus according to claim 2, wherein the reservoir includes a mouthwash formulated to be acceptable for oral administration, the mouthwash including an abrasive in a liquid carrier, such carrier being substantially non-foaming and including a surfactant.

4. An apparatus according to claim 3, wherein the surfactant is nonionic.

5. An apparatus according to claim 3, further including a defoamer.

6. An apparatus according to claim 3, wherein the abrasive is stably dispersed in the liquid carrier.

7. An apparatus according to claim 3, further comprising at least one of a non-foaming detergent; a suspension agent; a viscosity modifier; a stabilizing agent; a tartar control agent; and a therapeutic agent.

8. An apparatus according to claim 1, further comprising bristles disposed at the distal end of the head component.

9. An apparatus according to claim 1, further comprising an orifice boot coupled to the housing proximate to an opening in the distal end.

10. An apparatus according to claim 1, further comprising a one-way valve for initial purging of a volume of air between the pump drive mechanism and the flexible membrane.

11. An apparatus according to claim 1, wherein the pump drive mechanism includes a first and a second piston, both pistons driven in linear motion in a direction substantially perpendicular to the planar dimension of the flexible membrane.

12. An apparatus according to claim 11, wherein the pump drive mechanism includes two Scotch yokes for driving the pistons in a motion having a specified phase relation between positions of the two pistons.

13. An apparatus according to claim 12, wherein the first piston drives the flexible membrane in such a manner as to impel the cleaning fluid composition so as to exit at a distal end of the head component into the mouth of a user.

14. An apparatus according to claim 12, further including a first one-way valve for directing cleaning fluid composition between the flexible membrane and the distal end of the head component.

15. An apparatus according to claim 1, wherein an outer faring of the head component is made from material transparent to and capable of being sterilized by ultraviolet radiation.

16. An apparatus according to claim 15, wherein the ultraviolet radiation transparent material is a synthetic polymer.

17. An apparatus according to claim 16, wherein the synthetic polymer is selected from the group consisting of: an ionomer; a polycarbonate; and a polyethylene.

18. An apparatus according to claim 1, further comprising a sensor for actuating the pump when the apparatus contacts the surface.

19. An apparatus according to claim 1, further comprising a sensor for disabling the pump unless the distal end of the head is disposed within the mouth of a user.

20. An apparatus according to claim 1, wherein the head is made from material suitable for sterilization by exposure to microwave radiation.

21. A method for cleaning a surface in a mouth, the method comprising:
   providing a cleaning fluid in a reservoir;
   impelling the fluid from the reservoir and out of an exit nozzle toward a vicinity of the surface; and
   holding the exit nozzle in a position such that the pump urges the fluid from the vicinity of the surface back to the reservoir, for further impelling of the fluid toward the vicinity of the surface.

22. A method according to claim 21, wherein the cleaning fluid comprises a composition selected from the group of: a detergent and a defoaming agent; a non-foaming detergent; a defoaming agent; and a non-foaming detergent and a defoaming agent.

23. A method according to claim 21, wherein the cleaning fluid further comprises an abrasive agent.

24. A method according to claim 23, wherein the abrasive agent is characterized by a hardness between that of dentin and tooth enamel.

25. A method according to claim 24, wherein the abrasive agent is at least one selected from the group of: dicalcium phosphate dihydrate, insoluble sodium calcium pyrophosphate, calcium carbonate, alumina trihydrate, magnesium trisilicate, silica gel, precipitated silica, and a synthetic resin.

26. A method according to claim 23, wherein the fluid further comprises a shear thinning fluid matrix.

* * * * *

UNITED STATES PATENT AND TRADEMARK OFFICE
CERTIFICATE OF CORRECTION

PATENT NO.     : 6,375,459 B1
DATED          : April 23, 2002
INVENTOR(S)    : Dean L. Kamen et al.

It is certified that error appears in the above-identified patent and that said Letters Patent is hereby corrected as shown below:

Column 6,
Line 50, replace "dimension the" with -- dimension, the --.

Signed and Sealed this

Twenty-fourth Day of June, 2003

JAMES E. ROGAN
*Director of the United States Patent and Trademark Office*